(12) United States Patent
Chanduszko et al.

(10) Patent No.: US 10,299,906 B2
(45) Date of Patent: *May 28, 2019

(54) EMBOLUS BLOOD CLOT FILTER UTILIZABLE WITH A SINGLE DELIVERY SYSTEM OR A SINGLE RETRIEVAL SYSTEM IN ONE OF A FEMORAL OR JUGULAR ACCESS

(71) Applicant: C. R. BARD. INC., Murry Hill, NJ (US)

(72) Inventors: Andrzej J. Chanduszko, Chandler, AZ (US); Khoi Ta, San Jose, CA (US)

(73) Assignee: C. R. BARD, INC., Murray Hill, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/144,709

(22) Filed: May 2, 2016

(65) Prior Publication Data

US 2016/0317275 A1    Nov. 3, 2016

Related U.S. Application Data

(63) Continuation of application No. 12/303,545, filed as application No. PCT/US2007/070311 on Jun. 4, 2007, now Pat. No. 9,326,842.

(Continued)

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01);
(Continued)

(58) Field of Classification Search
CPC .................. A61F 2/01; A61F 2002/016; A61F 2002/018; A61F 2002/011;
(Continued)

(56) References Cited

U.S. PATENT DOCUMENTS 5,683,411 A * 11/1997 Kavteladze ........ A61B 17/0057
606/200
6,007,558 A * 12/1999 Ravenscroft .............. A61F 2/01
606/194

(Continued)

*Primary Examiner* — Katherine M Rodjom
(74) *Attorney, Agent, or Firm* — Garvey, Smith & Nehrbass, Patent Attorneys, L.L.C.; Seth M. Nehrbass; Charles C. Garvey, Jr.

(57) ABSTRACT

A blood filter delivery system for delivering a filter into a vein from either a femoral or jugular access. The preferred system includes an introducer and a push-rod with a spline member disposed along the push-rod and a pusher member disposed on a distal end. The spline member has a main body, first and second boss portions spaced apart along the longitudinal axis to provide a gap for retaining anchor members of the filter during delivery via the introducer. In an alternative embodiment, a preferred filter includes first and second filter structures diverging in opposite directions. A link is connected to portions of each of the first and second filter structures so that each filter structure can be independently collapsed into a generally cylindrical shape.

17 Claims, 10 Drawing Sheets

Related U.S. Application Data

(60) Provisional application No. 60/811,034, filed on Jun. 5, 2006.

(52) U.S. Cl.
CPC . *A61F 2210/009* (2013.01); *A61F 2210/0019* (2013.01); *A61F 2220/0016* (2013.01); *A61F 2230/0058* (2013.01); *A61F 2230/0078* (2013.01); *A61F 2310/00017* (2013.01); *A61F 2310/00023* (2013.01); *A61F 2310/00029* (2013.01); *A61F 2310/00047* (2013.01); *A61F 2310/00071* (2013.01); *A61F 2310/00077* (2013.01); *A61F 2310/00083* (2013.01); *A61F 2310/00149* (2013.01); *A61F 2310/00155* (2013.01); *A61F 2310/00287* (2013.01)

(58) Field of Classification Search
CPC ...... A61F 2230/0058; A61F 2210/0014; A61F 2210/0019; A61F 2220/0016
See application file for complete search history.

(56) References Cited

U.S. PATENT DOCUMENTS

| | | | | |
|---|---|---|---|---|
| 2001/0023358 A1* | 9/2001 | Tsukernik | ................. | A61F 2/01 606/200 |
| 2003/0114880 A1* | 6/2003 | Hansen | ................... | A61F 2/013 606/200 |
| 2003/0208227 A1* | 11/2003 | Thomas | .................... | A61F 2/01 606/200 |
| 2004/0082966 A1* | 4/2004 | WasDyke | ................. | A61F 2/01 606/200 |
| 2005/0004596 A1* | 1/2005 | McGuckin, Jr. | .......... | A61F 2/01 606/200 |
| 2006/0106417 A1* | 5/2006 | Tessmer | .................... | A61F 2/01 606/200 |
| 2008/0281149 A1* | 11/2008 | Sinai | ....................... | A61F 2/005 600/32 |

* cited by examiner

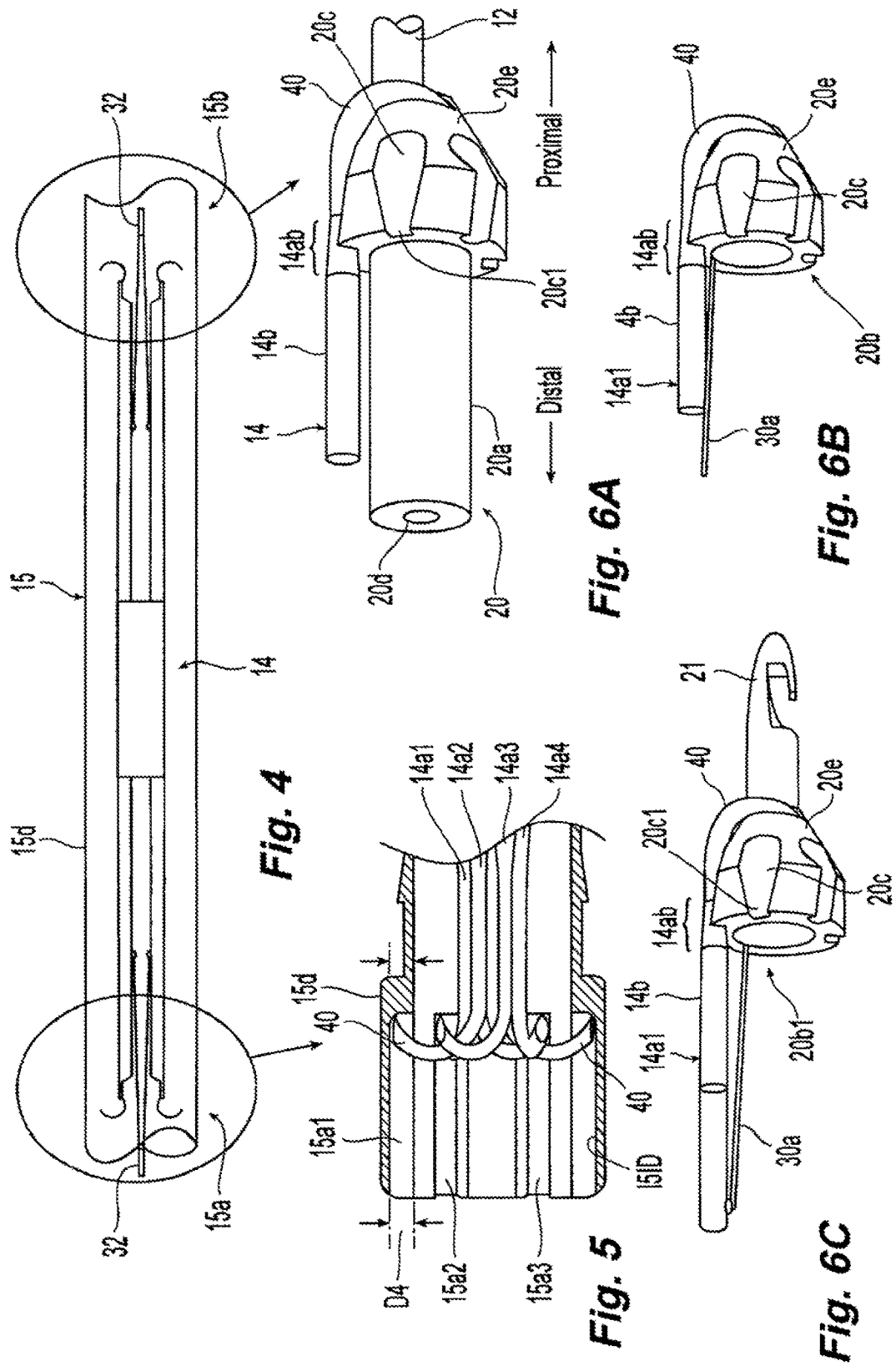

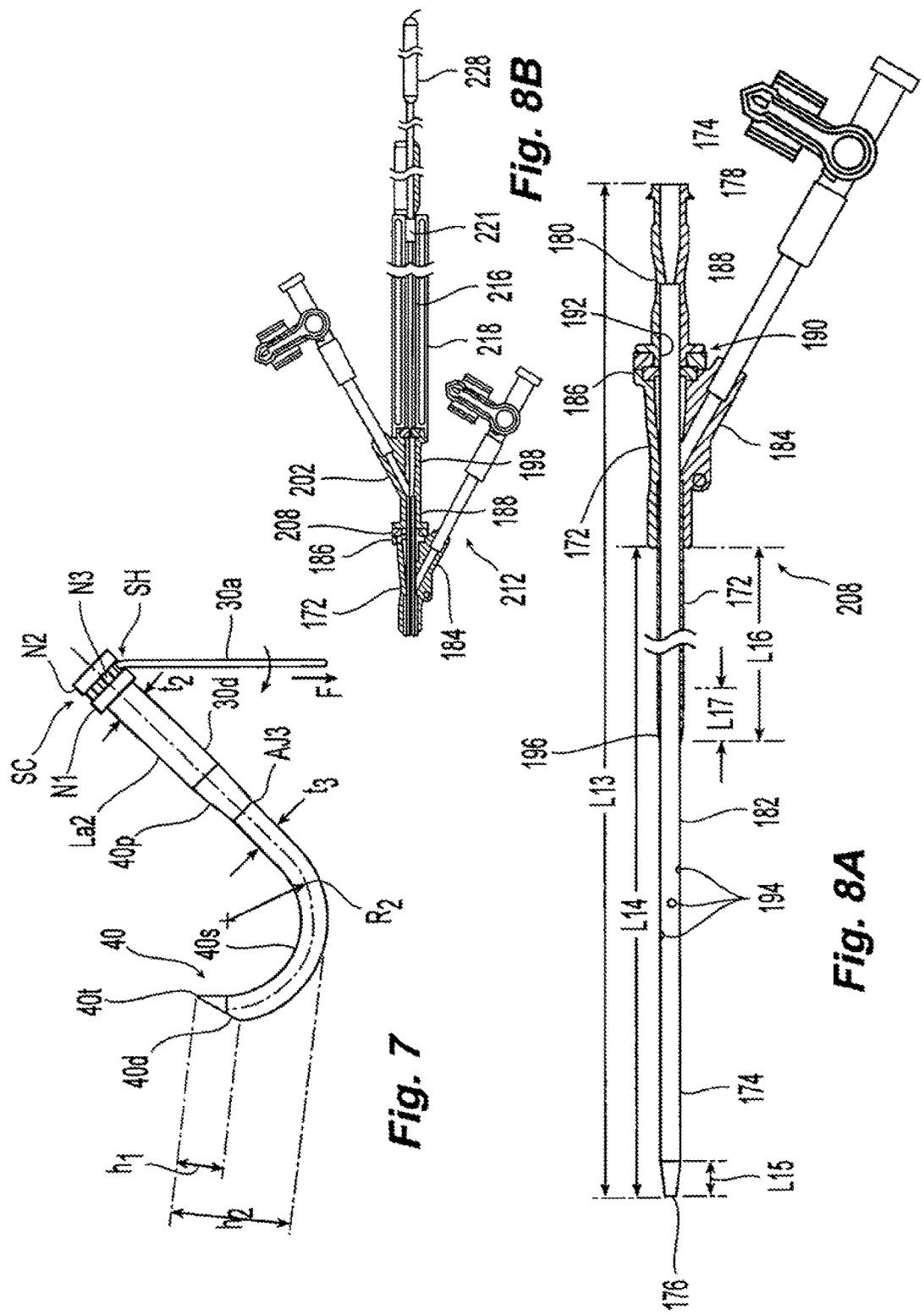

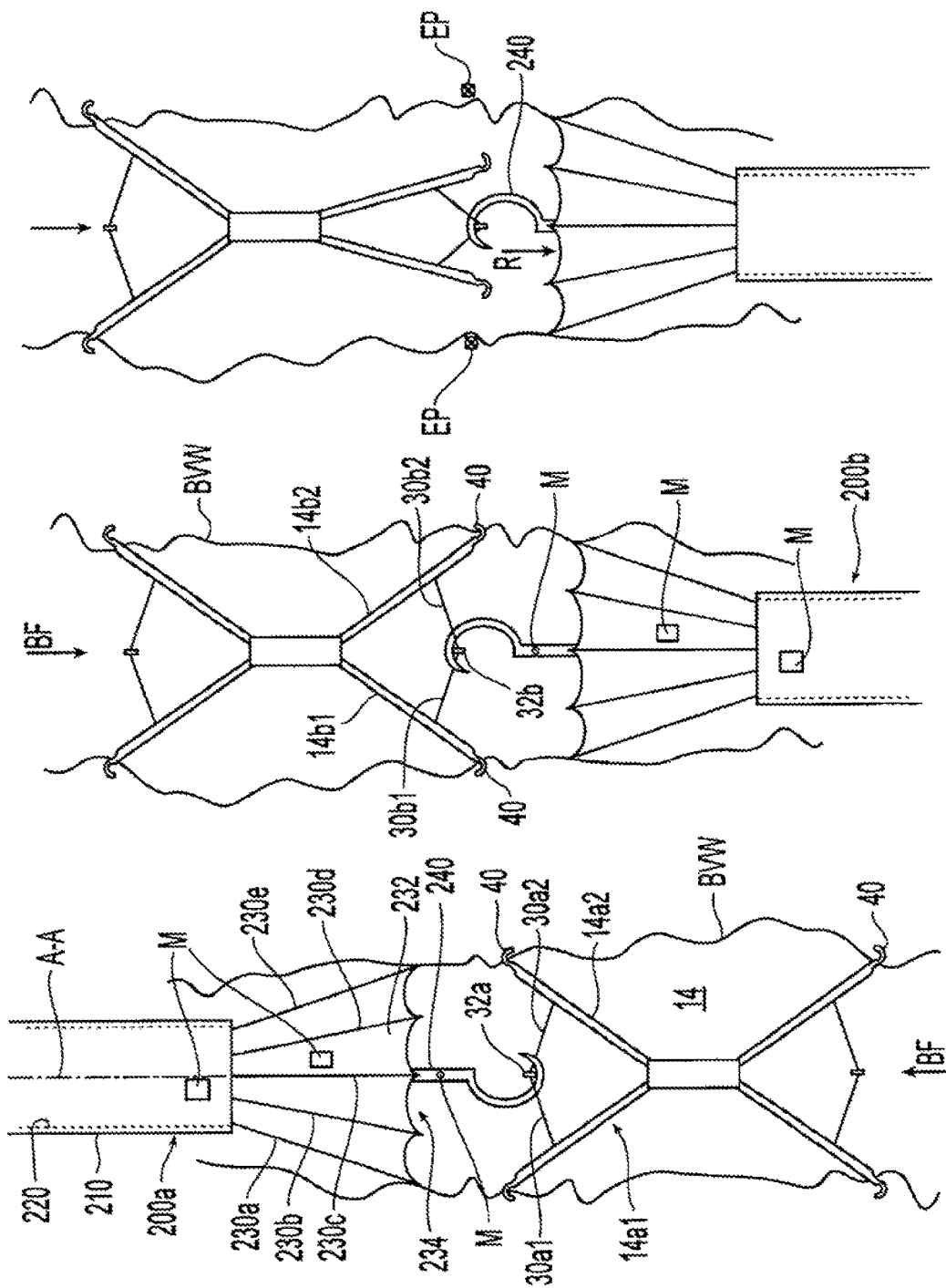

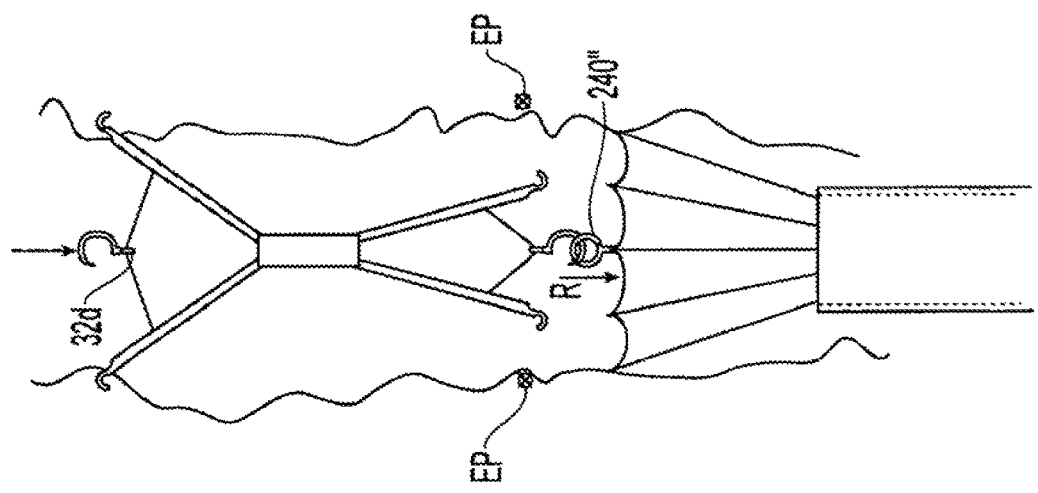
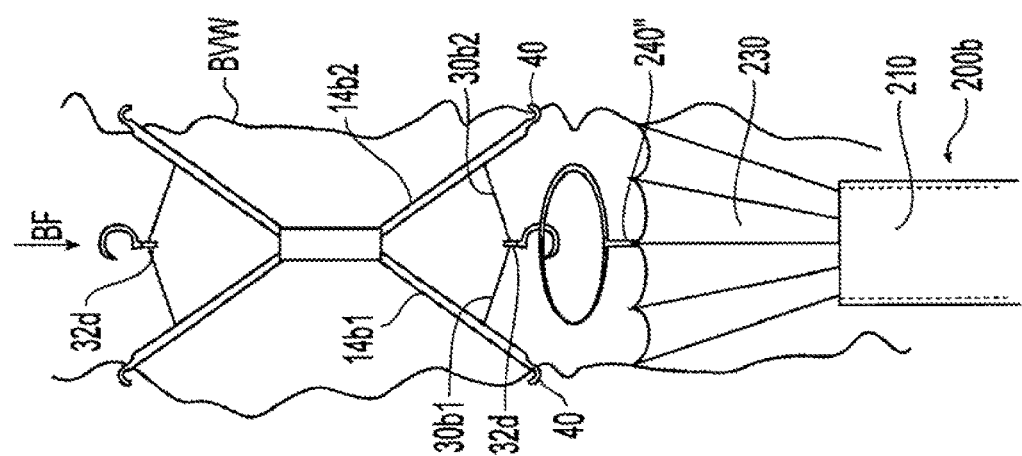

EMBOLUS BLOOD CLOT FILTER UTILIZABLE WITH A SINGLE DELIVERY SYSTEM OR A SINGLE RETRIEVAL SYSTEM IN ONE OF A FEMORAL OR JUGULAR ACCESS

PRIORITY

This application is a continuation of U.S. patent application Ser. No. 12/303,545, filed Jun. 29, 2009, now U.S. Pat. No. 9,326,842, which is a U.S. national stage application under 35 U.S.C. § 371 of International Application No. PCT/US2007/070311, filed Jun. 4, 2007, which claims the benefit of priority to U.S. Provisional Patent Application No. 60/811,034, filed Jun. 5, 2006, each of which is incorporated by reference in its entirety.

BACKGROUND

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein, such as the vena cava. These vena cava filters are generally designed to remain in place permanently. Such filters include structure to anchor the filter in place within the vena cava, such as elongate diverging anchor members with hooked ends that penetrate the vessel wall and positively prevent migration in either direction longitudinally of the vessel. The hooks on filters of this type are rigid, and within two to six weeks after a filter of this type has been implanted, the endothelium layer grows over the diverging anchor members and positively locks the hooks in place. Any attempt to remove the filter results in a risk of injury to or rupture of the vena cava.

A number of medical procedures subject the patient to a short-term risk of pulmonary embolism, which can be alleviated by a filter implant. In such cases, patients are often averse to receiving a permanent implant, for the risk of pulmonary embolism may disappear after a period of several weeks or months. However, most existing filters are not easily or safely removable after they have remained in place for more than two weeks, and consequently longer-term temporary filters that do not result in the likelihood of injury to the vessel wall upon removal are not available.

It is believed that most of the known filters are not capable of being delivered without regard for the orientation of the filter or access site. It is also believed that most of the known filters are not capable of being retrieved in either one of a femoral or jugular approach with one retrieval device.

One of the known filters, described and shown in U.S. Pat. No. 6,251,122 issued to Tsukernik, utilizes a plurality of strands with a sliding member slidingly disposed about a portion of the strands. Recovery of this filter, however, is believed to require two different devices approaching from both the femoral and jugular access sites as shown in FIG. 4 of this patent.

Another known filter, described and shown in U.S. Pat. No. 6,443,972 as a somewhat symmetrical filter. However, this filter, like others, can only be retrieved from one access site.

Applicants have recognized that biological anatomies may vary such that access from the jugular may be inappropriate or that access from a femoral site is similarly inappropriate. For example, in the known filter delivery system, if the jugular (or femoral) site is inappropriate for delivery and the delivery system of a known filter can only be utilized from the jugular (or femoral) approach then the clinician would have to obtain a femoral Jugular) delivery system. To provide immediate access to an alternative delivery device during a procedure, this would require the clinician to have two systems in the clinical inventory prior to the procedure. Similarly, in the known delivery system, if the retrieval is inappropriate for the jugular (or femoral) approach then the clinician would have to obtain a femoral (or jugular) retrieval system prior to the procedure. Immediate access to one or the other retrieval systems would require a clinical inventory of two different retrieval systems prior to the procedure. Hence, applicants have recognized the desirability for a blood filter system that addresses one or more of the above issues.

SUMMARY

Various embodiments described and illustrated herein relates to a blood filter device, delivery system, and retrieval system for such blood filtering device in a blood vessel.

The various embodiments provide for a blood filter utilizable with a blood filter delivery or retrieval system that resolves potential problems of the known delivery system and filter and have therefore advance the state of the art in blood filter designs, blood filter delivery and retrieval techniques.

In one embodiment, a blood filter is provided that includes first and second filter structures, and a link. The first and second filter structures diverge away from a longitudinal axis in opposite directions in a first configuration of the filter structures. The link is connected to discrete portions of each of the first and second filter structures so that each filter structure is independently collapsed into a generally cylindrical shape in a second configuration.

In yet another embodiment, a delivery catheter sheath for a blood filter is provided that includes a generally tubular member. The generally tubular member has a first end, intermediate end and a second end defining a longitudinal axis extending therethrough. The first end has an inner surface exposed to the longitudinal axis; the inner surface has a plurality of notches formed on the inner surface; the intermediate end includes a boss portion disposed in the tubular member, which has a plurality of grooves formed in the boss portion.

In a further embodiment, a blood filter retrieval device is provided that includes first and second generally tubular members, a collapsible member and a retrieval member. The first generally tubular member extends from a first end to a second end to define a longitudinal axis extending therethrough. The second generally tubular member can be disposed generally coaxially with the first generally tubular member. The collapsible member can be coupled to the second generally tubular member that defines a portion of a cone in one configuration and a cylinder in another configuration. The retrieval member can be disposed in the second tubular member and the collapsible member.

In yet another embodiment, a blood filter system is provided that includes an introducer, pusher assembly, and a blood filter. The introducer may have a coupling port connected to an elongated generally tubular member. The pusher assembly may have a first end disposed in the storage member and a second end extending out of the Y-adapter and further include a handle disposed along a longitudinal axis of the pusher assembly proximate the second end; a pusher disposed along the longitudinal axis proximate the first end of the elongated assembly; and a generally tubular member having a first end, intermediate end and a second end defining a longitudinal axis extending therethrough, the first end having an inner surface exposed to the longitudinal axis, the inner surface having a plurality of notches formed on the inner surface, the intermediate end including a boss portion coupled to the pusher and disposed in the tubular member having a plurality of grooves formed in the boss portion, the first end coupled to the Y-adapter. The blood filter may include at least a first anchor member having hooks disposed in one of the grooves and notches; and at least a second anchor member having hooks disposed in the other of the grooves and notches.

In yet an alternative embodiment, a blood filter kit is provided that includes a delivery system, blood filter, and instructions for use. The delivery system includes: an introducer having a coupling port connected to an elongated generally tubular member; a dilator configured to be inserted into the introducer to dilate a vessel; a pusher assembly having a first end disposed in the storage member and a second end extending out of the Y-adapter and further having: a handle disposed along a longitudinal axis of the pusher assembly proximate the second end; a pusher member disposed along the longitudinal axis proximate the first end of the elongated assembly; and a generally tubular member having a first end, intermediate end and a second end defining a longitudinal axis extending therethrough, the first end having an inner surface exposed to the longitudinal axis, the inner surface having a plurality of notches formed on the inner surface, the intermediate end including a boss portion coupled to the pusher and disposed in the tubular member having a plurality of grooves formed in the boss portion, the first end coupled to the Y-adapter. The blood filter includes at least a first anchor member having hooks disposed in one of the grooves and notches; at least a second anchor member having hooks disposed in the other of the grooves and notches. The instructions on how to deliver the blood filter to a site in a human readable graphical and textual format using the delivery device.

In yet a further embodiment, a method of delivering a blood filter from either an incision in the femoral or jugular vessels is provided. The method can be achieved by providing a filter, storing such filter, accessing an implant site, and releasing the filter from the sheath proximate the implantation site to engage the filter structures against a vessel wall of the implantation site. The blood filter may have first and second filter structures that diverge away from a longitudinal axis in opposite directions in a first configuration with a link connected to discrete portions of each of the first and second filter structures so that each filter structure is independently collapsed into a generally cylindrical shape in a second configuration. The filter is stored proximate a distal end of a generally tubular sheath having a first end, intermediate end and a second end defining a longitudinal axis extending therethrough. The first end may have an inner surface exposed to the longitudinal axis. The inner surface may have a plurality of notches formed on the inner surface. The intermediate end includes a boss portion coupled to the pusher and disposed in the tubular member having a plurality of grooves formed in the boss portion. The implantation site may be accessed via one of the femoral or jugular vessels.

DRAWINGS

The accompanying drawings, which are incorporated herein and constitute part of this specification, illustrate presently preferred embodiments of the invention, and, together with the general description given above and the detailed description given below, serve to explain features of the invention.

FIG. 4 illustrates one of the filters as disposed in the sheath of the delivery system in a close up view.

FIG. 5 illustrates a distal end of the sheath in which various retention members of the filter are located in notches.

FIG. 6A illustrates a proximal end of the sheath in which various retention members of the filters are located in a splined member, which is not part of the filter.

FIG. 6B illustrates a splined member that is part of the filter.

FIG. 6C illustrates yet another splined member that is part of the filter with a recovery member provided on the splined member.

FIG. 7 illustrates, in a close up view, one embodiment of a retention member.

FIGS. 8A and 8B illustrate details of another embodiment of a delivery sheath for a filter delivery system.

FIGS. 9A-9I illustrate exemplarily a high level overview of a filter retrieval process using one embodiment of a retrieval system.

FIGS. 11A-11B illustrate exemplarily a high level overview of another filter retrieval process using a third embodiment of the retrieval system.

DESCRIPTION OF EXEMPLARY EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

Figure 3:
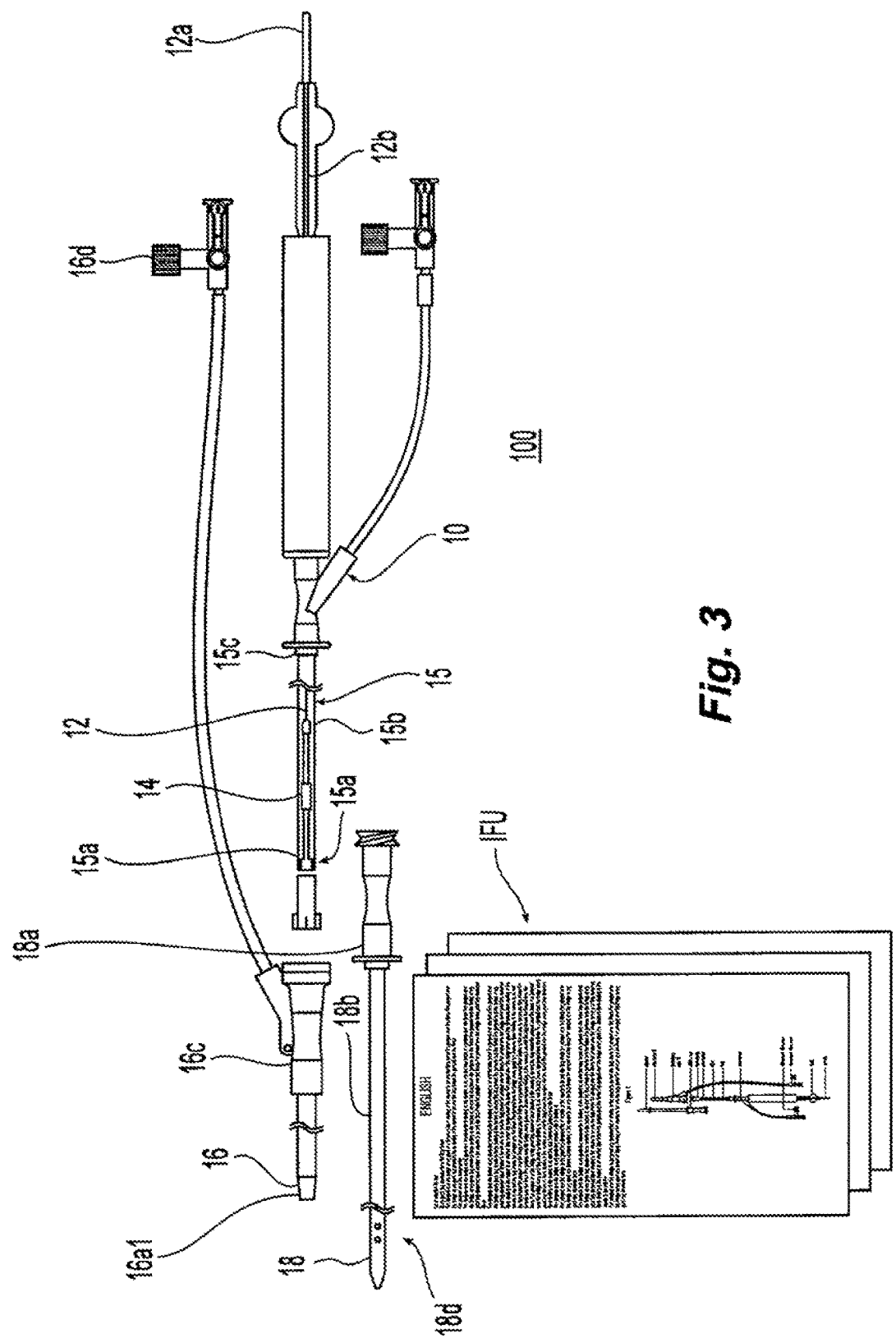
FIG. 3 illustrates a delivery system for one of the embodiments of blood filter including instructions for use embodied in paper form.

FIGS. 1-11 illustrate one of many exemplary embodiments. In an overview, as shown in FIG. 3, a blood filter system 100 includes a Y-adapter 10, catheter sheath 15 containing the filter 14, a catheter-like introducer 16 and a pusher assembly 12 to push the filter 14 from the catheter sheath 15, through the introducer 16 and then into the blood vessel. For convenience in illustrating the preferred embodiments, the blood filter system 100 has various components that can be referenced to an imaginary longitudinal axis A-A. Each system is preferably packaged as a "kit" with instructions-for-use IFU for sale to a clinician. Each component of the blood filter system is described in greater detail below.

Referring back to FIG. 1, one exemplary embodiment of the blood filter 14 is illustrated in its first or operational configuration in a blood vessel BY, which has a blood vessel wall BVW disposed about a blood flow path BF.

As implanted, the blood filter 14 may include first and second filter structures 14a and 14b that diverge away from a longitudinal axis A-A in opposite directions in the implanted configuration, as shown here in Fig. I. First filter structure 14a may have at least two anchor members 14a1 and 14a2. Similarly, second filter structure 14b may have at least two anchor members 14b1 and 14b2. Each of the anchor members can include a retention member 14h disposed at a terminal end thereof, such as, for example, a barbed hook, a curved hook or a double barbed hook.

In the preferred embodiments, the first and second filter structures can be integrated with each other. For example, with reference to FIG. 1, a single wire can be configured to have three sections: a first section defining a portion of the first filter structure, a middle section disposed proximate the longitudinal axis, and a second section defining a portion of the second filter structure. As such, for a filter utilizing four anchor members for each of the filter structures, four wires can be utilized. The wires can be bent into the first section, middle and second sections and joining the respective middle sections of the wires together. At the junctures J1 and J2 for the middle and first sections and middle and second sections, a small radius of curvature can be provided to reduce stress concentration at the respective junctures J1 and J2 in the wire. Although the term "wire" herein is utilized to denote an elongated member having a generally circular cross-section, other members formed by suitable techniques with different cross-sections can be utilized. For example, a plurality of wires can be formed by extrusions or by laser cutting a thin tubular form. In the preferred embodiments, a shape memory material such as, for example, Nitinol can be utilized. Other materials can be used instead of Nitinol, such as, for example, shape memory materials (e.g., copper alloy systems (Cu—Zn; Cu—Zn-AI) and alloys of Au—Cd, Ni-AI, Fe—Pt, or shape memory stainless steel), shape memory composites, weak shape memory metals (e.g., stainless steel, platinum, Elgiloy), shape memory polymers, bioresorbable metals, polymers, piezoelectric ceramics (e.g. barium titanate, lead zirconate to name a few), piezoelectric composites, sputter deposited Ni—Ti films, magnetostrictive materials, magnetic shape memory materials, nanocomposites, electroactive polymers that undergo shape change in the presence of voltage potentials.

In the preferred embodiments, the wire can be a material selected from a group consisting essentially of shape memory material, super-elastic material, linear-elastic material, metal, alloys, polymers and combinations thereof. Preferably, the wire has a cross-sectional area of about 0.00013 squared inches.

Figure 1:
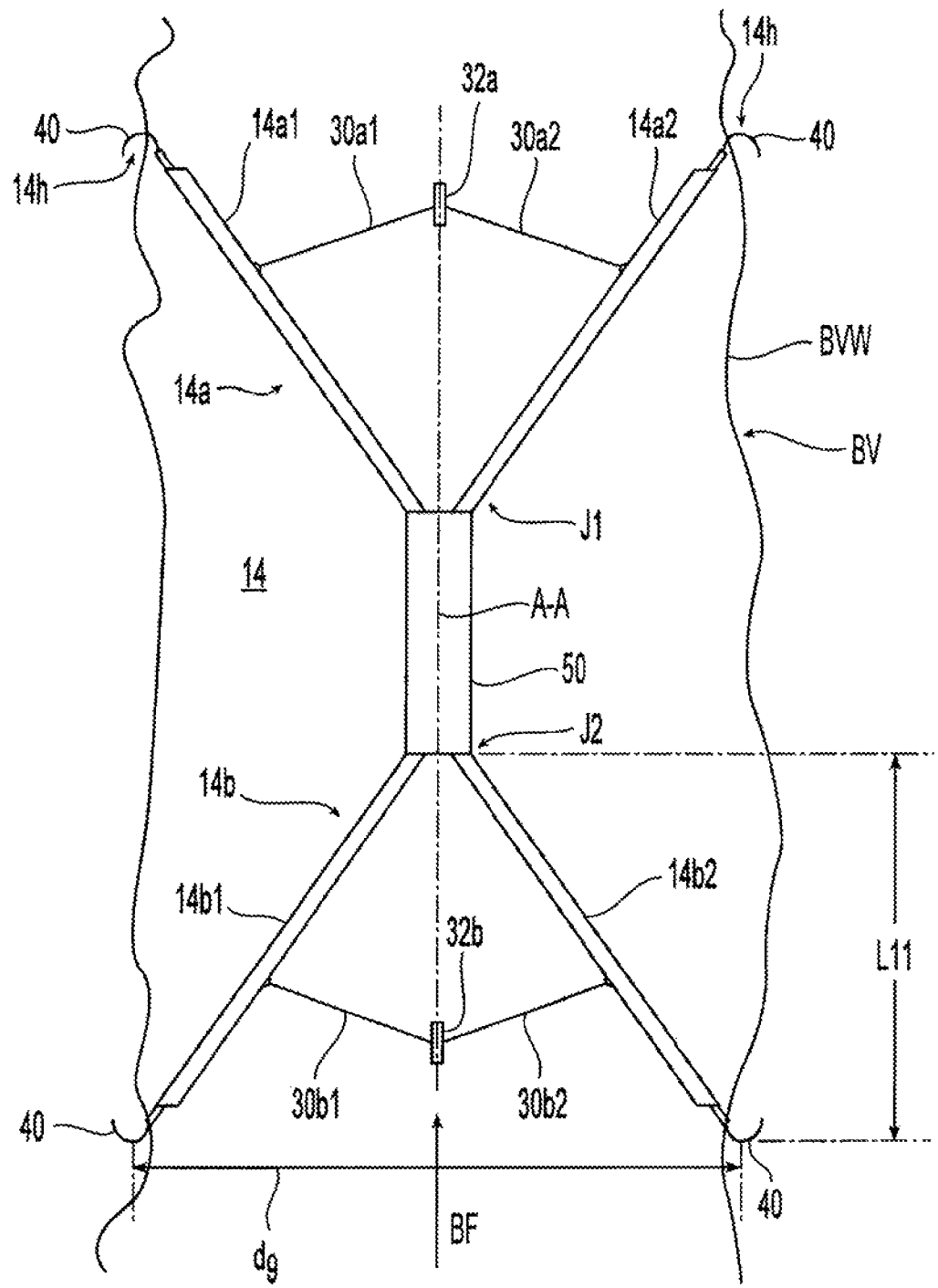
FIG. 1 illustrates exemplarily a first embodiment of a blood filter.
Figure 2:
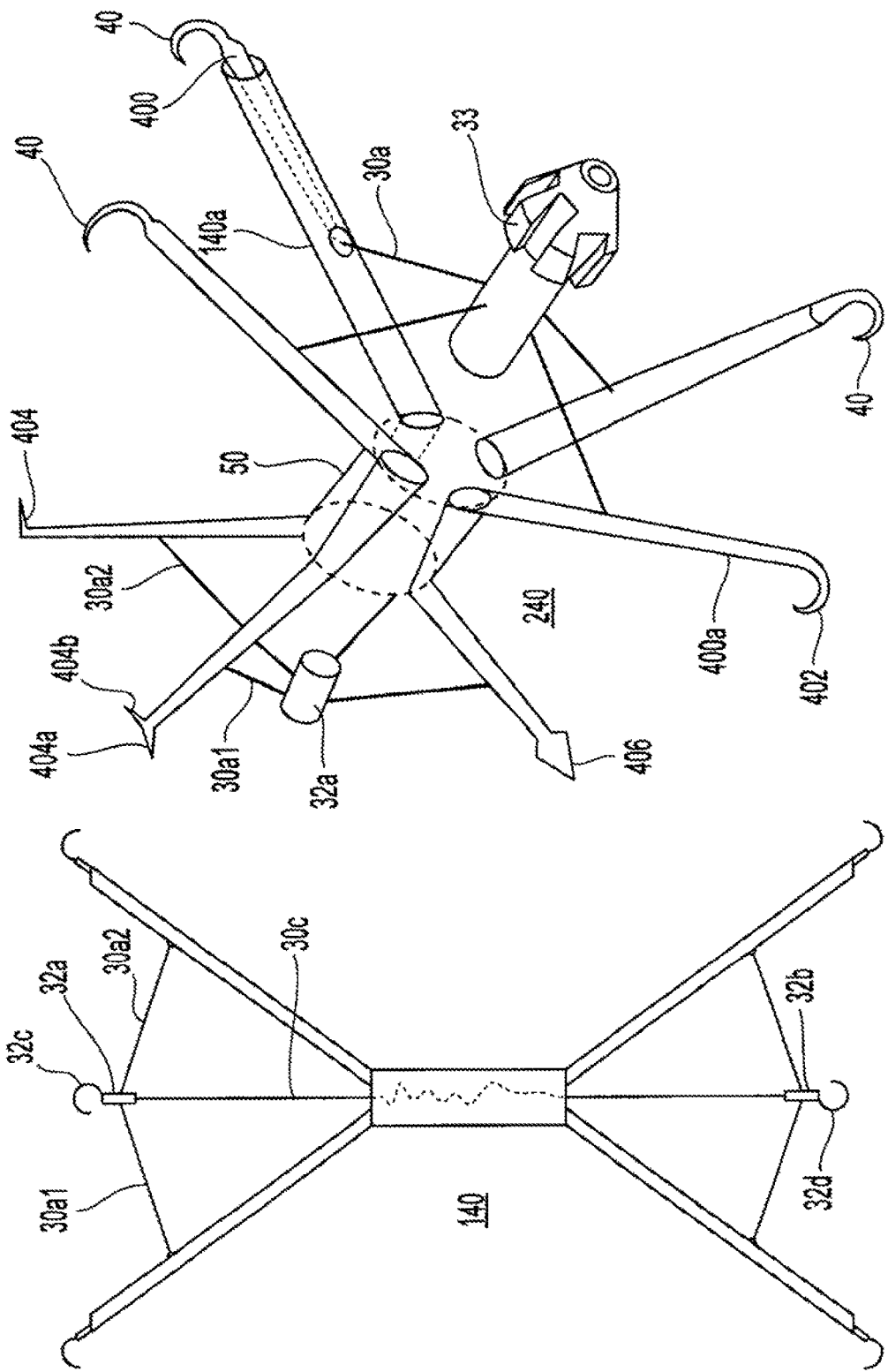
FIG. 2A illustrates exemplarily a second embodiment of a blood filter.
FIG. 2B illustrates exemplarily a plurality of embodiments of the blood filter.

Instead of joining the wires together proximate the middle sections of the wires, a hub 50 can be utilized to constrain the plurality of wires forming the first and second filter structures, as shown here in FIG. 1. Hub 50 can be coupled to the middle sections by a suitable coupling technique such as, for example, swaging, crimping, welding, bonding, gluing. Hub 50 can be a porous polymer loaded with suitable bio-active agents for elution once filter 14 has been implanted.

Instead of making the filter out of wires, a blood filter of generally the same configuration can be cut out from a thin tubular member using a suitable cutting technique such as, for example, laser cutting (as described and shown in U.S. Pat. No. 6,099,549, which is incorporated by reference herein in its entirety), electric-discharge machining or via etching.

Each of the filter structures 14a and 14b preferably respectively has a link 30a and link 30b, as shown in FIG. 1, which allows each of the filter structures 14a and 14b to be independently collapsed into a generally cylindrical shape in a second or non-operational configuration. The link preferably includes an elongated member connected to the first section of each wire of the first filter structure via a suitable connection, such as, for example, a welded, or a swivel coupling SC, shown here in FIG. 7 with boss portions N1 and N2 to constrain link 30a to anchor portion 30d via a circular hoop N3 so that as a force F is applied, link 30a and anchor 30d rotate relative to each other. That is, the swivel coupling SC allows the link 30a and wire or anchor 30d to rotate relative to each other. Where a hinged connection is desired, a super-elastic coupling SH can be employed in place or interposed between link 30a and loop N3 of the swivel coupling. The super-elastic coupling SH can be, for example, a super elastic hinge such as one shown and described in U.S. Pat. No. 5,776,162 to Kleshinski, issued Jul. 7, 1998, which document is herein incorporated by reference in its entirety. Alternatively, a sliding coupling can be utilized by integrating N1, N2 and N3 together and configuring these members to slide and rotate with respect to anchor 30d. In yet a further alternative, the super-elastic coupling SH can be integrated with the sliding coupling.

Referring again to FIG. 1, one or both of the links 30a, 30b for the filter structures 14a, 14b can include another elongated member connected to the first section of each wire of the filter structures 14a, 14b. More specifically, one or both of the links 30a, 30b can be respectively connected to a hub 32a, 32b. The hubs 32a, 32b are preferably located substantially along the longitudinal axis A-A. Although each of the first and second filter structures are illustrated as having at least two elongated members, it is within the scope of this disclosure to have a single unitary link connecting all of the anchor members (e.g., 2-8 anchor members) together to allow the anchor members to be configured into the collapsed shape such as, for example, shown in FIG. 3.

Each link can be coupled to the anchor member anywhere along the length of the anchor member including any portions proximate the hook 40. Preferably, the link is anchored at a suitable distance from the hook 40 so that tissue in-growth does not substantially prevent the link from swiveling or pivoting. In a preferred embodiment, the link can be made out of a material other than the material or materials in which the filter anchor member is made of. For example, the link can be made out of suture material (resorbable and non-resorbable type) or carbon nanotubes or metal wire.

Variations of the filter 14 can be utilized by a clinician for delivery and extraction. For example, as shown in FIG. 2A, the links are interconnected via a third link 30c extending through hollowed hub 50 so that upon full collapsing of one filter section will lead to the partial or full collapse of the other filter section. That is, one link is interlocked to the other link. Additionally, the hub 32a or 32b can be provided with a retrieval member 32c or 32d for this embodiment.

Several alternative configurations are exemplarily illustrated in FIG. 2B. In a first configuration, anchor member 140a can be a partially hollow tube with retention member 400 disposed in a telescopic manner. The retention member 400 is preferably provided with a hook 40 that can be straightened as the anchor member 140a is pulled into the tube by a spline member 33. In this configuration, the links 30a are connected to retractable super elastic hooks 42 for respective anchor members, which can range in quantity from 3, 4, 6, 8 or 12 members. The connection allows the hooks to be partially or even fully retracted into hollow anchor members 14a1, 14a2, 14a3, 14a3 when the spline member 33 (or nub 32A) is pulled or pushed along the longitudinal axis. Another embodiment is also illustrated in which the retention member 400a does not utilize smaller cross-sectional area hook 402 as with hook 40. Instead of curved hooks, another embodiment would include linearly angled member 404. Alternatively, more than one linearly angled member 404 can be used as shown here with members 404a and 404b. In yet a further embodiment, an arrow shaped retention member 406 can be utilized.

In the preferred embodiments, retention member 14h is a curved hook 40 that extends for at least forty-five degrees (45°) about a center, and in one variation, the hook can subtend for more than three hundred and sixty degrees (360°) about a center. In the preferred embodiments, the hook 40 can be made from material selected from a group consisting essentially of shape memory material, super-elastic material, linear-elastic material, metal, alloys, polymers and combinations thereof.

Most preferably, the hook 40 is of the configuration shown in FIG. 7 with a proximal hook portion 40p and a distal hook portion 40d on which a sharpened tip 40t is provided. The hook 40 can be formed to have a thickness $t_3$. Where the hook 40 is formed from a wire having a generally circular cross-section, the thickness $t_3$ may be generally equal to the outside diameter of the wire. In an embodiment, the hook thickness $t_3$ is approximately 0.5 to approximately 0.8 that of the anchor thickness $t_2$. The wire can be configured to follow a radius of curvature $R_2$ whose center is located at longitudinal distance L11 and radial distance d9 when the filter is at the temperature of a subject, as discussed above. The tip 40t can be provided with a generally planar surface whose length can be approximately equal to length $h_1$. The tip 40t may be located over a distance $h_2$ from a plane tangential to the curved portion 40s. Preferably, the hook is a curved member having a cross-sectional area of about 0.000086 squared inches (in.$^2$).

Of particular interest is the ability of the preferred hook to take on a curved configuration in an operative condition and towards a generally linear configuration in another condition when axial force is applied along the length of the wire. Details of this ability of the hook (and the pusher assembly along with a similar catheter assembly) are shown and described in U.S. Pat. No. 6,258,026 issued Ravenscroft et at on Jul. 10, 2001; U.S. Pat. No. 6,007,558 issued to Ravenscroft et at on Dec. 28, 1999, provisional application Ser. No. 60/680,601 filed on May 12, 2005, and as well as in a PCT Patent Application that claims priority to the antecedent provisional patent application, which PCT Patent Application is entitled "Removable Embolus Blood Clot Filter," having PCT Publication No. WO 2006/124405 filed on May 9, 2006, which documents are incorporate herein by reference in their entirety.

The filter 14 can be delivered or implanted using a delivery system 100, illustrated in FIGS. 3-6A that includes a catheter sheath 15 containing the filter 14. Components of the system include an adapter, such as a Y-adapter, and in particular, a Touhy-Borst Adapter 10 (FIG. 3), a catheter sheath 15 (FIG. 5) coupled to the Touhy-Borst Adapter 10 with a filter 14 stored in the catheter sheath 15, and provided with an elongated pusher assembly 12 that can be used to deploy the filter 14 in a blood vessel of a mammal. Other components that can be used with the system include a catheter introducer 16 and a catheter dilator 18.

Referring to FIG. 3 and FIG. 5, the delivery catheter sheath 15 can include a generally tubular member having a first end 15a, intermediate end 15b, and a second end 15c (FIG. 3) defining a longitudinal axis A-A extending therethrough the generally tubular member 15d. The first end 15a preferably has an inner surface 151D exposed to the longitudinal axis, where the inner surface 151D has a plurality of notches 15a1, 15a2, 15a3 formed on the inner surface 151D (FIG. 5). The plurality of notches 15a1-15a3 are preferably configured to engage the hooks 40 of the anchor members 14a1-14a4 to facilitate symmetrical loading of the filter 14. To provide for the plurality of notches 15a1-15a3, the first end 15a is preferably enlarged compared to the remainder of the tubular member 15d. Elimination of the enlarged end 15a can provide for an optional lower profile sheath 15 in instances where symmetrical loading is not necessary.

The intermediate end 15b (FIG. 6A) may include a boss portion 20a disposed in the tubular member 15 having a plurality of grooves 20c formed in the boss portion 20 having a truncated conical surface 20e on which filter hooks 40 (with only one shown for clarity in FIG. 6A) can be mounted thereon with a portion of transition portion 14ab being secured in the groove 20c. Each groove 20c of can be provided with a plurality of widths along a longitudinal length of the groove to provide for various gaps in the groove. The anchor portion of the filter 14 is configured to have a maximum width greater than a minimum width of the groove 20c so that the anchor portion is limited in its longitudinal movement in groove 20c. This feature allows for the splined boss 20 to move anchor portion 14b in the distal direction (leftward in FIG. 6A) when splined boss 20 is moved distally (leftward in FIG. 6A).

The splined boss 20 can be connected to the pusher 12 so that axial movement of the pusher distally would cause the filter 14 to be pushed out of catheter sheath 15 for delivery into the blood vessel. The splined boss 20 may be provided with an opening 20d so that nub 32a or 32b can be inserted into the opening while the filter 14 is in a pre-delivery configuration in sheath 15. Alternatively, the catheter sheath 15 may include a housing or body coupled at the second 15c end of the sheath 15 while an elongated member 12 can be used to push a boss portion 20b, which is part of the filter (FIG. 6B). In yet a further alternative, a boss portion 20b1 (which is part of filter 14) can be provided with a retrieval member 21 as shown, for example, in FIG. 6C.

Each of the various embodiments of the splined boss 20 is utilized to maintain the hooks 40 in a non-interference configuration, i.e., non-crossed configuration, while the filter 14 is in the sheath 15. In these embodiments, the splined boss is utilized to transmit motion in the distal direction from the handle 12a into the anchor members 14a1, 14a2, and 14a3 and so on during delivery of the filter out of the sheath 15 into the blood vessel. The splined boss achieves this by having various cross-sectional areas of the groove 20c where at least one cross-sectional area of the groove is smaller than the smallest cross-sectional area (e.g. 14ab) of the anchor member 14*a*1 (but exclusive of the cross-sectional area of the hooks 40, which is smaller than any of the above). Further, where the splined boss is integral with the pusher 12, the boss is designed so that movement of the splined boss 20 in the proximal direction while in the sheath 15 is restrained so that substantial inadvertent movement of the pusher 12 in the proximal direction does not result in the filter 14 being pulled towards the Y-adapter 10.

In the configurations of FIG. 3, the elongated member 12 extends from the one end through another end of the body to provide a portion that can be utilized as a handle 12*a*. In the preferred embodiments, the body is a Y-adapter 10 with a marker disposed proximate the first end of the sheath. The elongated member 12 includes a generally cylindrical member 12*b* having at least two different cross-sectional areas, e.g., a larger diameter portion. For example, distal of the handle 12*a*, the elongated member 12 can have a stainless steel tube (not shown) disposed about the cylindrical member 12*b* to allow for sufficient rigidity while being handled by a clinician while still allowing for flexibility proximate the tip when navigating a tortuous blood vessel. Also preferably, the sheath IS includes a polymeric tube having at least two different Shore durometer of hardness proximate one of the first and second ends.

The hooks of the preferred embodiments allow for removal of the filter 14 with minimal injury to a blood vessel. In particular, with reference to FIG. 7, the hook 40 can be provided with a proximal hook portion 40*p* and a distal hook portion 40*d* on which a sharpened tip 40*t* is provided. The hook 40 can be formed to have a thickness t3. Where the hook 40 is formed from a wire having a generally circular cross-section, the thickness t3 may be generally equal to the outside diameter of the wire. In an embodiment, the hook thickness t3 is approximately one-half that of the anchor thickness t2. The wire can be configured to follow a radius of curvature R2 whose center is located at longitudinal distance L II and radial distance d9 when the filter is at the temperature of a subject, as discussed above. The tip 40*t* can be provided with a generally planar surface 40*d* whose length can be approximately equal to length h1. The tip 40*t* may be located over a distance h2 from a plane tangential to the curved portion 40*s*. Preferably, the radius of curvature R2 is about 0.03 inches and the thickness t2 of the anchor member is about 0.013 inches.

Once implanted, the hooks 40 may be removed from the Inferior Vena Cava ("IVC") wall during filter removal procedure when longitudinal force is applied to the hub 50 in the direction of the BF. Under this concentrated stress, the hooks will tend to straighten and transition to the martensitic state, thereby becoming super-elastic. Thus the hooks 40 are designed to bend toward a substantially straight configuration as seen, for example in FIG. 9H, when a specific hook migration force is applied and spring back to their original shape once the hook migration force is removed. By virtue of this design, the hooks 40 will tend to leave a small generally circular incision EP in the vessel wall as the hooks are super elastically straightened (without suffering from catastrophic failure) during removal rather than a large gash or tear in the vessel wall, as is the case with known hooks that do not utilize the features discussed herein.

Alternatively, a reduction in temperature below an Af temperature can be applied to the shape memory material to cause a change in the crystalline phase of the material so as to render the material malleable during loading or retrieval of the filter. Various techniques can be used to cause a change in crystalline phase such as, for example, cold saline, low temperature fluid or thermal conductor.

In another embodiment, shown in FIG. 8A, a dilator 174 and introducer sheath 172 (that are similar to the dilator and introducer of FIG. 3) can be interlocked together and operated as a single unit 208. In this example, the overall length L13 of the combined unit is about 26 inches; the length L14 of the dilator 174 measured from the base of the fluid infusion hub to a tip 176 of the dilator is about 24 inches; the length L15 of the tapered tip portion of the dilator 174 is about 0.2 inches; the length L16 of the introducer sheath 172 measured from the base of the fluid infusion hub to the tip 196 of the sheath is about 21 inches; and the length L17 of the tapered distal portion of the introducer sheath is about 0.2 inches. Side ports 194 are provided along the length of the distal portion of the dilator such that fluid infused through the dilator 174 may exit the side ports 194 and dilate the blood vessel or provide contrast agent for real-time imaging of the dilator tip. The dilator/introducer sheath unit 208 may then be inserted over a suitable sized guidewire into the patient's circulatory system. Once the distal end 196 of the introducer sheath 172 is placed at the desired location in the blood vessel, the surgeon may disengage the dilator 174 from the introducer sheath 172 and withdraw the dilator 174 and the guidewire from the lumen of the introducer sheath 172.

FIG. 8B illustrates a proximal end of the introducer sheath 186 engaged with the fluid infusion hub 202 on the delivery catheter 198 so as to interlock the two devices together. As shown, a block-stop 221 is positioned within a channel 216 in the delivery hub extension housing 218. The block-stop 221 prevents the user from over withdrawal of the pusher member 228. Moreover, the block stop 221 can prevent the pusher member 228 from backing out in the proximal direction during shipping. As shown in FIG. 8B, when the pusher member 228 is fully displaced in the proximal direction, the stop member 221 abuts the proximal wall of the delivery hub extension 218 and prevents further withdrawal of the pusher member 228. Optionally, the stop member 221 may be configured with a cross-sectional profile, such as square, that matches the inner surface of the delivery hub extension housing 218 to prevent the pusher member 228 from rotating. This anti-rotational mechanism may be particularly useful to prevent rotation of the filter and/or entanglement of the legs. However, in a design utilizing a pusher 12, such as the one shown in FIG. 3, an anti-rotational mechanism is not necessary.

In the preferred embodiments, a kit is provided that includes the filter delivery system 100 along with instructions IFU for a clinician to deliver the filter to a target site in a host. The instructions on delivery of the filter can include the following guidelines.

i. A suitable femoral or jugular venous vessel site in the host may be selected. Typically, this is the vessel on either the left or right side, depending upon the patient's size or anatomy, the clinician's preference and/or the location of a venous thrombosis.

ii. The site can be nicked with a blade and the vein punctured with a suitable entry needle, such as an 18-gage needle, or trocar.

iii. A suitable guidewire, such as a J-tipped guidewire, is inserted into the needle and advanced into a distal vena cava or iliac vessel where a filter is to be delivered. Once the guidewire is in position, the entry needle is removed from the patient and slipped off the proximal end of the guide wire.

iv. The dilator 18 is inserted into the introducer 16. Then the proximal end of the guidewire is inserted into both the introducer 16 and dilator 18. Saline or a suitable biocompatible fluid is provided to the introducer valve 16*d* to remove air in the introducer 16, and then the assembly is inserted into the patient and advanced along the guidewire until it reaches a desired position in the vena cava or iliac vessel. Positioning of the introducer tip 16*a*1 within the vein at the site for delivering the filter may be confirmed by fluoroscopy, aided by the radio-opaque markers on or within the introducer 16. Contrasting agent or dye can also be provided to the ports 18*d* (or 194 of FIG. 8A) of the dilator tube 18*b* via the dilator body 18*a* to provide for visual imaging of the introducer tip 16*a*1 via suitable fluoroscopic imaging equipment. The guidewire and the dilator 18 can be removed once the user or physician has determined that the introducer tip 16*a* I is at the desired location in the vein or vessel.

v. The dilator 18 can be separated from a snap-fit of the introducer 16 by bending and pulling the two components. The introducer can be left with its tip in the vena cava. Fluid can be introduced into the introducer via valve 16*d*.

vi. The filter 14, which is pre-stored in the catheter sheath 15, can be coupled to the coupling port 16*b* via the snap-fitting, and saline can be permitted to flow through the catheter sheath 15 to provide lubricity between various components of the delivery system 100. The saline may be chilled during portions of the procedure. Similarly, the saline may be warmed during portions of the procedure, such as just prior to releasing the filter into the vein, to help raise the filter and pusher assembly 12 components above the martensitic-to-austenitic transition temperature, causing the filter to seek its annealed shape. The introducer 16, catheter sheath 15 and elongated pusher assembly 12 are preferably held in a linear configuration to avoid kinking and minimize friction. The filter 14 is physically advanced from the catheter sheath 15 through the introducer 16 to a position near the distal tip 16*a*1 of the introducer 16. The advancement of the filter 14 can be accomplished by maintaining the introducer 16 stationary while pushing on the handle 12*a* of the elongated pusher assembly 12 in the distal direction. The filter 14 is maintained inside the introducer 16, i.e., undeployed at this point. Markings on the pusher assembly 12 may permit the clinician to determine the position of the filter 14 with respect to the end of the introducer 16. Additionally, fluoroscopy may be used to track the position of the filter 14 within the introducer 16 and with respect to the patient. When the filter hub 50 approaches the distal end of the introducer 16, the filter is ready to be deployed.

vii. To deploy the filter 14, the elongated pusher assembly 12 and the introducer hub 16*c* are moved relative to each other over a first predetermined distance. At this point, the introducer 16 is retracted proximally while the pusher 12 is held in stationary position to allow the anchor members 14*b*1-14*b*5 to become unconstrained by the introducer sheath 16*a* and free to expand radially. Hooks 40 at the ends of the anchor members 14*b*1-14*b*5 begin to dig or penetrate into the blood vessel wall to maintain the filter 14 at approximately the desired location.

It should be noted that the instructions IFU for the kit could be embodied in any suitable format such as, for example, in paper or electronic forms (e.g., a web site, PDFs, video or audio).

Figure 9G:
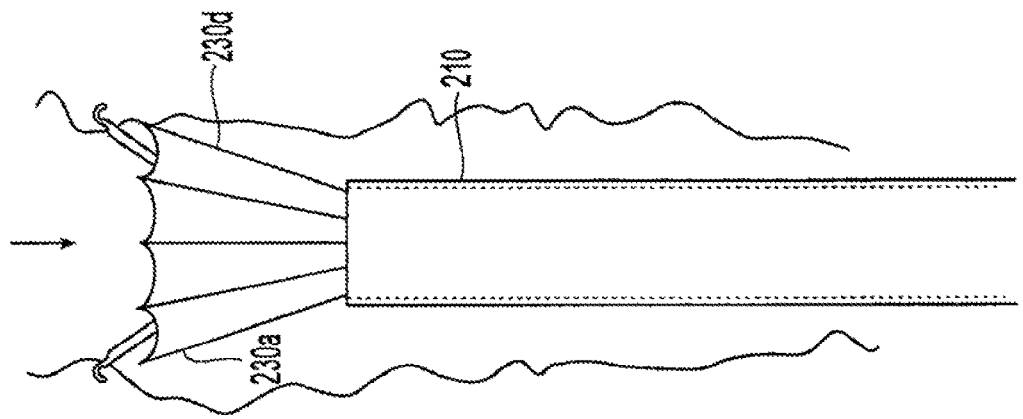
Figure 9F:
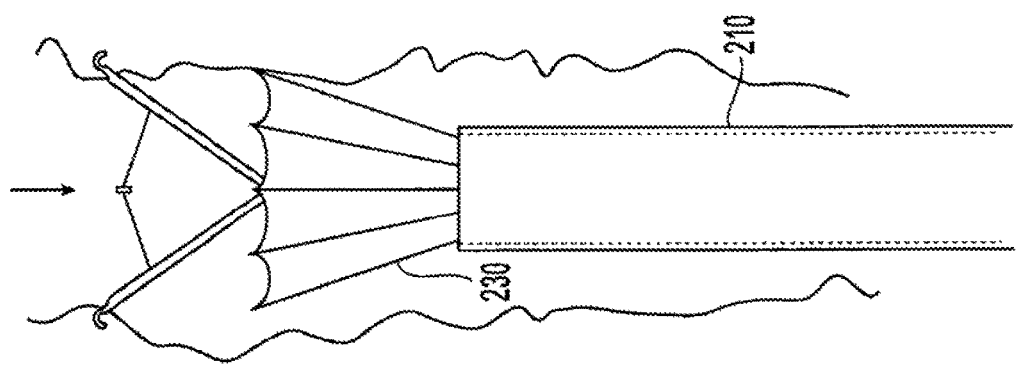
Figure 9E:
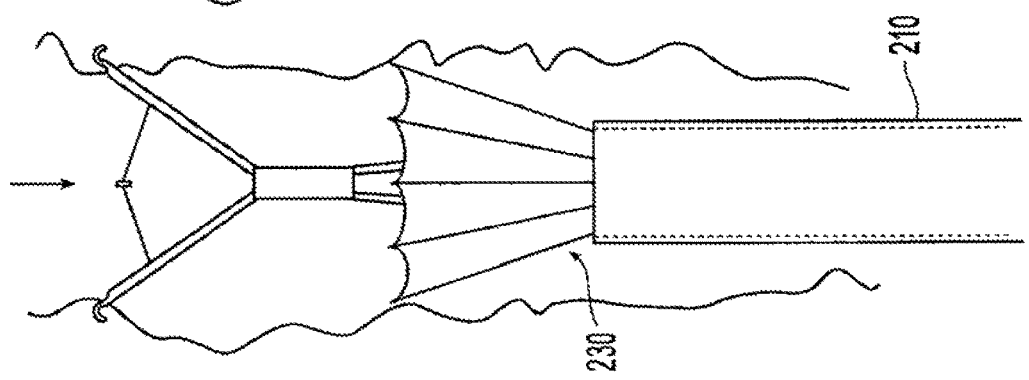
Figure 9D:
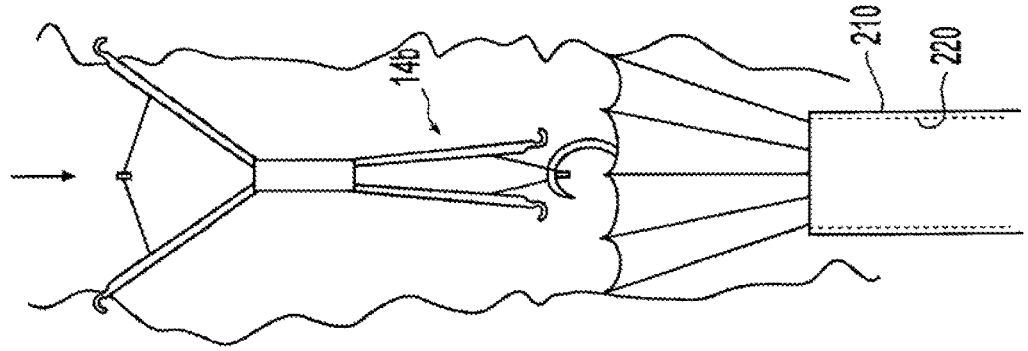
Figure 9I:
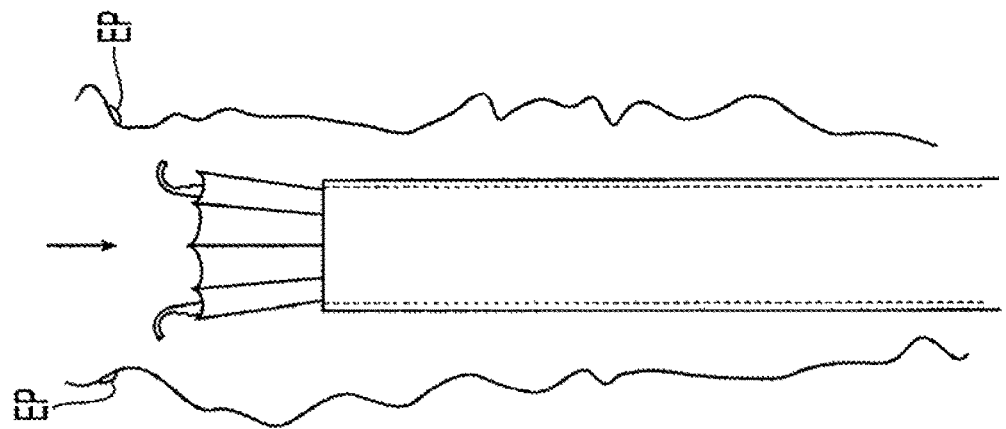
Figure 9H:
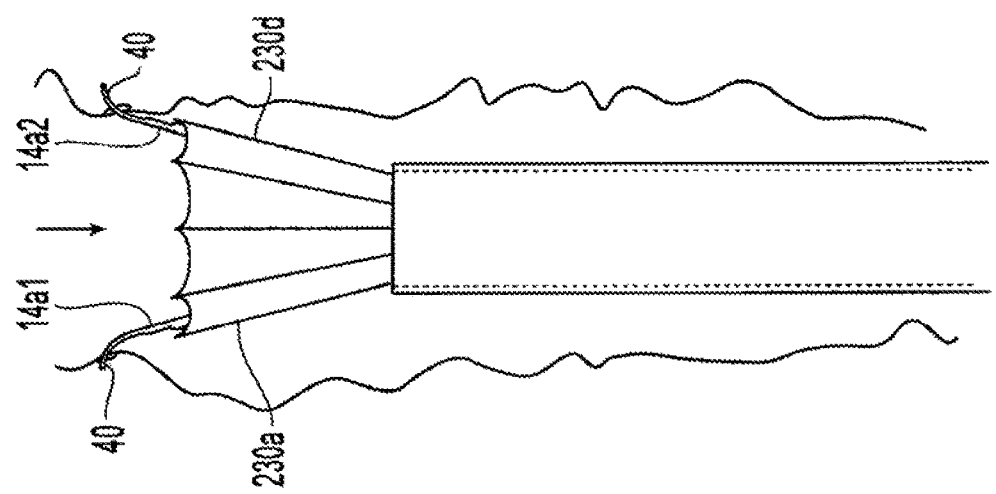
Figure 10A:
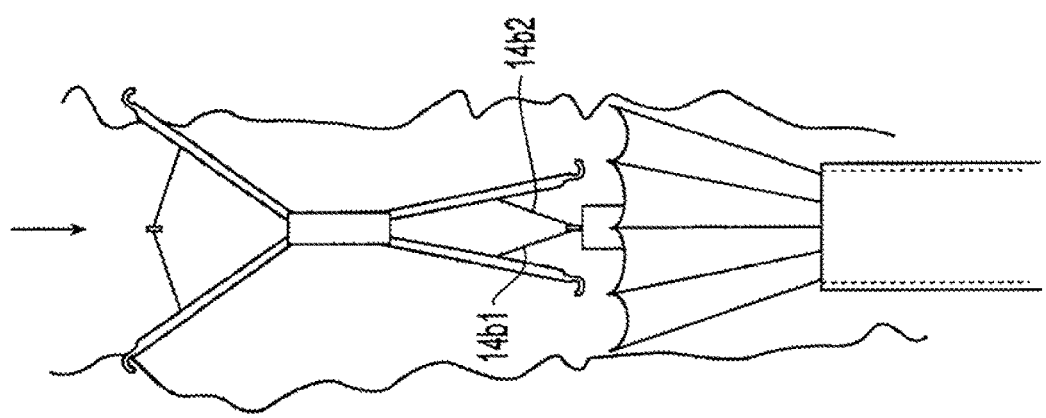
FIGS. 10A-10B illustrate exemplarily a high level overview of yet another filter retrieval process using a second embodiment of the retrieval system.
Figure 10B:
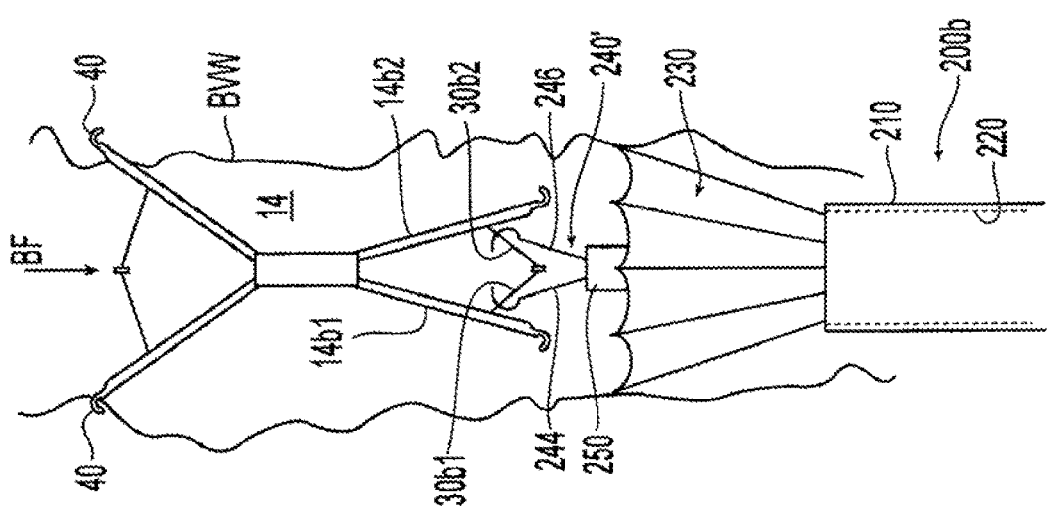

To recover the filter 14, there are at least three different embodiments of a recovery device suitable to remove filter 14. The first embodiment is shown in FIGS. 9A-9I whereas the second embodiment is shown in FIGS. 10A-10B and the third embodiment is shown in FIGS. 11A-11B. Each embodiment is discussed in turn below. It should be noted that both embodiments could be utilized to remove the filter either from a jugular or a femoral approach.

Referring to FIG. 9A, the recovery device 200*a* is graphically illustrated as being utilized from a jugular approach. Alternatively, the recovery device 200*b* can be utilized from a femoral approach, illustrated here based on the direction of blood flow BF in FIG. 9B. The retrieval device may include first and second generally tubular retrieval sheaths or members 210 and 220 where the first generally tubular member 210 extends from a first end to a second end to define a longitudinal axis A-A extending therethrough, and the second generally tubular member 220 is disposed generally coaxially with the first generally tubular member 210. The retrieval device 200*a* may also include a collapsible member 230 coupled to the second generally tubular member 220 that defines a portion of a cone in a first configuration (FIG. 9A) and a cylinder (FIG. 9I) in another configuration where a retrieval member 240 is disposed in the second tubular member 220 and the collapsible member 230. The retrieval member 240 in this embodiment includes at least one claw 242. Markers M can be provided in at least one or more of the components described in relation to FIGS. 9A, 10A and 11A.

As shown in FIG. 9A, the collapsible member 230 can be configured as a plurality of radially extending members 230*a*-230*d* connected together via a membrane 232 to define a generally truncated cone 234 in a deployed configuration of the retrieval device 200*a*. The membrane can be made from suitable material such as, for example, (and not limited to) ePTFE, Dacron, polyurethane, polytetrafluoroethylene, nylon, PET, PEBAX, barium sulfate, and combinations thereof. To assist a clinician in determining the location of the retrieval device in relation to the filter, a radiopaque marker can be disposed on at least one of the first, second and third tubular members.

Retrieval can be performed as follows. In FIG. 9B, the retrieval member 240 is maneuvered into position so that it engages the links 30*b*1 and 30*b*2 (or 30*a*1 and 30*a*2 if the retrieval device is utilized with the jugular approach). Instead of a nub, the splined member with retrieval hook 21 (FIG. 6C) can be utilized with a retrieval member in the configuration of a looped snare, shown for example, in the preferred embodiment of FIGS. 11A-11B. Proximal movement R of the retrieval member 240 results in the links being pulled in the proximal direction which results in the extraction of hooks 40 from the vessel wall BVW. The extraction of the hooks 40 generally leaves very small incision opening on the vessel wall that are slightly larger than the cross-sectional area of each hook with little or almost no tear or injury to the vessel wall. As the retrieval member 240 is continued to be pulled relative to the retrieval sheaths (or the retrieval sheaths 210 and 220 are moved distally while the retrieval member 240 is stationary), shown here in FIGS. 9D and 9E, the filter structure 14*b* is converted from a generally conic configuration towards a generally cylindrical configuration. The sheaths 210 and 220 are moved distally once the filter structure 14*b* is in the cylindrical configuration. The sheaths 210 and 220 continue to move distally towards filter structure 14*a*, shown here in FIGS. 9F and 9G. Continued movement of the sheaths 210 and 220 will cause the collapsible member 230 to engage the anchor members 14*a*1 and 14*a*2 (FIGS. 9G and 9H) at which point the membrane 232 or the radially extending members 230*a*-230*d* causes the filter structure 14*a* to collapse into a cylindrical configuration, which causes the hooks 40 to straighten and explant from the vessel wall with small incision points EP. Continued relative movement of the sheaths 210, 220 relative to retrieval member 240 causes the filter 14 to be retracted into the collapsible member 230. In one preferred embodiment, the entire filter 14 and collapsible structure are retracted within the sheath 210 and the sheaths 210 and 220 are removed from the blood vessel.

In the second embodiment illustrated in FIGS. 10A and 10B, the retrieval device 200b includes a third sheath or generally tubular member 250 disposed about a portion of retrieval member 240' where the retrieval member 240' includes plurality of claws 244 and 246. Retrieval of the filter is performed by engaging the claws 244 and 246 against links 30b1 and 30b2. The claws 244, 246 are pulled into the third sheath 250 to force the claws to move toward each other and thereby capture the links therebetween. Once the claws are retracted into the third sheath 250, the third sheath 250 is moved relative to the collapsible member 230 (i.e., the sheath 250 can move relative to stationary sheaths 210 and 220 or sheaths 210, 220 can move relative to sheath 250). Extraction of the filter can be performed in a manner similar to FIGS. 9F-9I.

In the third embodiment illustrated in FIGS. 11A and 11B, the retrieval device 200b includes retrieval member 240" having a collapsible looped snare, such as for example, an Amplatz GOOSE NECK snare from eV3 Inc., preferably configured to engage the retrieval hook 21 of the filter 14, as shown for example, in FIG. 6C. Retrieval of the filter is performed by engaging the looped snare of the retrieval member 240" with the retrieval hook 21 of the filter 14. Proximal movement R of the retrieval member 240" results in the links being pulled in the proximal direction which results in the extraction of hooks 40 from the vessel wall BVW. Extraction of the filter can be performed in a manner similar to FIGS. 9F-9I. It should be noted that the three extraction methods described herein can also be embodied as instructions-for-use with the retrieval system as a kit, in somewhat of a similar configuration as the delivery kit.

By virtue of the filter, delivery system and retrieval system described herein, a method of delivering a filter and extracting such filter can be provided. In particular, the method allows for delivery of a blood filter from either an incision in the femoral or jugular vessels. The method can be achieved by providing a filter having first and second filter structures that diverge away from a longitudinal axis in opposite directions in a first configuration and a link connected to discrete portions of each of the first and second filter structures so that each filter structure is independently collapsed into a generally cylindrical shape in a second configuration; storing the filter proximate a distal end of a generally tubular sheath having a first end, intermediate end and a second end defining a longitudinal axis extending therethrough, the first end having an inner surface exposed to the longitudinal axis, the inner surface having a plurality of notches formed on the inner surface, the intermediate end including a boss portion coupled to the pusher and disposed in the tubular member having a plurality of grooves formed in the boss portion; accessing an implantation site via one of the femoral or jugular vessels; and releasing the filter from the sheath proximate the implantation site to engage the filter structures against a vessel wall of the implantation site. Retrieval of the filter can be performed by forming an access to the implantation site via one of the femoral or jugular vessels; and retrieving the filter into a retrieval sheath. The retrieving can include retracting a portion of at least one hook from one of the filter structures to disengage the hook from the vessel wall.

In another embodiment, bio-active agents can be incorporated with the blood filter or filter delivery system, such as by way of a coating on parts of the filter delivery components (e.g., the pusher member 12c or the tip of the introducer sheath 16a), or dissolvable structures on, within or attached to the filter delivery components. Alternatively, bio-active agents can be delivered to the region of the filter at the time of the filter emplacement by means of the introducer, either before or after delivery of the filter. Bio-active agent can be included as part of the filter delivery system in order to treat or prevent other conditions (such as infection or inflammation) associated with the filter, or to treat other conditions unrelated to the filter itself. More specifically, bio-active agents may include, but are not limited to:

pharmaceutical agents, such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine);

antiplatelet agents such as G(GP) lib/IIIa inhibitors and vitronectin receptor antagonists;

anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), and trazenes-dacarbazinine (DTIC);

anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine});

platinum coordination complexes (cisplatin, carboplatin), procarbazine, hydroxyurea, mitotane, aminoglutethimide;

hormones (i.e. estrogen);

anti-coagulants (heparin, synthetic heparin salts and other inhibitors of thrombin);

fibrinolytic agents (such as tissue plasminogen activator, streptokinase and urokinase), aspirin, dipyridamole, ticlopidine, clopidogrel, abciximab;

antimigratory agents;

antisecretory agents (e.g., breveldin);

anti-inflammatory agents, such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin);

para-aminophenol derivatives i.e. acetaminophen;

indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate);

immunosuppressives: (cyclosporine, tacrolimus (FK-506), sirolimus (rapamycin), azathioprine, mycophenolate mofetil);

angiogenic agents, such as vascular endothelial growth factor (VEGF), fibroblast growth factor (FGF);

angiotensin receptor blockers;

nitric oxide donors;

anti-sense oligonucleotides and combinations thereof;
cell cycle inhibitors, such as mTOR inhibitors, and growth factor receptor signal transduction kinase inhibitors; retenoids;
cyclin/CDK inhibitors;
HMG co-enzyme reductase inhibitors (statins);
and protease inhibitors.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®) fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference in its entirety, is particularly desirable. Another material can also be a copolymer of poly lactic acid and polycaprolactone.

While the present invention has been disclosed with reference to certain preferred embodiments, numerous modifications, alterations, and changes to the described embodiments are possible without departing from the sphere and scope of the present invention, which is described, by way of example, in the appended numbered paragraphs below. Accordingly, it is intended that the present invention not be limited to the described embodiments, but that it have the full scope defined by the language of at least the following paragraphs, and equivalents thereof.

The invention claimed is:

1. A blood filter comprising:
a first filter structure comprising at least two first-filter elongated members, each first-filter elongated member having a free end;
a second filter structure comprising at least two second-filter elongated members, each second-filter elongated member having a free end portion;
a juncture structure in between said first and second filter structures;
said first and second filter structures and said juncture structure having a central longitudinal axis;
a first-filter-structure link comprising a first-filter-structure tether and a first longitudinally movable hub wherein the tether connects between a said first-filter elongated member and said first longitudinally movable hub;
a second-filter-structure link comprising a second-filter-structure tether and a second hub wherein the tether connects between a said second-filter elongated member and said second longitudinally movable hub;
wherein each tether connects to a said filter elongated member at a position in between said juncture structure and a said free end portion;
wherein said first and second filter structures are sized and shaped to occupy a patient's blood vessel in a first, deployed configuration in which an outer end of the first-filter elongated members diverges from said longitudinal axis and an outer end of the second-filter elongated members diverges from said longitudinal axis;
wherein said first-filter elongated members and said second-filter elongated members extend in opposite directions from said juncture structure;
wherein said first and second filter structures each have a second collapsed configuration in which the elongated members are collapsed into a generally cylindrical shape;
wherein each said first and second filter structures are independently collapsible to said collapsed configuration that generally aligns said links with said longitudinal axis; and
wherein in said second, collapsed configuration, said longitudinally movable hubs are moved apart in opposite directions and said first-filter and second-filter elongated members and said links align generally with said central, longitudinal axis.

2. The blood filter of claim 1, wherein there is at least one elongated anchor member at said free end portion.

3. The blood filter of claim 2, wherein each of the first-filter elongated members connect to a corresponding second-filter elongated member with a wire that includes at least a portion of the first filter structure, said juncture structure, and a second section that includes a portion of the second filter structure.

4. The blood filter of claim 3, where each first-filter-structure link connects to a first section of each wire.

5. The blood filter of claim 4, wherein each second-filter-structure link connects to a second section of each wire.

6. The blood filter of claim 3, further comprising a spline-member attached to said first-filter-structure link and wherein there are multiple said anchor members, each of the anchor members comprises a tubular member having an open end and a hook having a portion disposed in the open end and connected to said first-filter-structure link so that the hook is partially retractable into the open end responsive to movement of the spline member, wherein said first-filter-structure link comprises a plurality of first-filter-structure tethers, each said first-filter-structure tether connected to a said anchor member or hook at one end and to a spline via the first hub at an opposite end.

7. The blood filter of claim 6, further comprising a boss connected to the first-filter-structure link.

8. The blood filter of claim 6, wherein said juncture structure includes a third hub disposed about the middle portion of the wires.

9. The blood filter of claim 3, wherein a said anchor member is disposed at one terminal end of each wire.

10. The blood filter of claim 3, wherein the wire comprises a material selected from a group comprising shape memory material, super-elastic material, linear-elastic material, metal, alloys, polymers and combinations thereof.

11. The blood filter of claim 3, further comprising a hook disposed in an end of each of the anchor members and connected to the first-filter-structure link so that the hooks are partially retractable.

12. The blood filter of claim 11 wherein the hooks further comprise a curved end and a straight end and the first-filter-structure link connects to the straight end.

13. The blood filter of claim 12 wherein the first-filter-structure link slidably and rotatably connects to the straight end.

14. The blood filter of claim 2, wherein the anchor member comprises a hook having a material selected from a group comprising shape memory material, super-elastic material, linear-elastic material, metal, alloys, polymers and combinations thereof.

15. The blood filter of claim 14, wherein the hook comprises a curved configuration in an operative condition and a generally linear configuration in another condition.

16. A delivery catheter sheath and blood filter assembly, including the blood filter of claim 1, the assembly comprising:
- a generally tubular member having a central longitudinal axis and a lumen;
- a first end;
- an intermediate end section;
- a second end, the first end having a plurality of notches formed on an inner surface, and the intermediate section including a grooved boss portion disposed in the tubular member, said blood filter having multiple anchors that each connect with a groove of the grooved boss;
- said blood filter contained in said lumen of said tubular member;
- a pusher connected to the boss so that axial movement of the pusher distally enables delivery of the filter into the blood vessel of a patient; and
- wherein the grooved boss has at least one groove with a cross sectional area that is smaller than at least one cross sectional area of the anchor.

17. The delivery catheter sheath and blood filter assembly of claim 16, wherein the pusher is coupled to the boss portion, the pusher extending out of an end of the generally tubular member to provide a handle.

* * * * *